United States Patent
Joung (10) Patent No.: US 7,323,688 B2
(45) Date of Patent: Jan. 29, 2008

(54) NUCLEAR IMAGING SYSTEM USING ROTATING SCINTILLATION BAR DETECTORS WITH SLAT COLLIMATION AND METHOD FOR IMAGING USING THE SAME

(75) Inventor: Jinhun Joung, Algunquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/879,902

(22) Filed: Jun. 29, 2004

(65) Prior Publication Data

US 2005/0285042 A1    Dec. 29, 2005

(51) Int. Cl.
*G01T 1/161* (2006.01)

(52) U.S. Cl. .................................. 250/363.02
(58) Field of Classification Search ............ 250/363.02
See application file for complete search history.

(56) References Cited

U.S. PATENT DOCUMENTS

| 3,688,113 | A | * | 8/1972 | Miraldi ..................... 250/366 |
| 4,514,632 | A | | 4/1985 | Barrett |
| 4,563,583 | A | | 1/1986 | Hattori |
| 6,521,894 | B1 | * | 2/2003 | Iwanczyk et al. ....... 250/370.11 |
| 6,710,349 | B2 | * | 3/2004 | Shao ....................... 250/363.03 |
| 6,762,413 | B2 | * | 7/2004 | Zeng ....................... 250/363.1 |
| 7,238,946 | B2 | | 7/2007 | Joung et al. |

2005/0029461 A1 * 2/2005 Malmin .................... 250/367

OTHER PUBLICATIONS

D. Gagnon, et al., "Design considerations for a new solid-state gamma-camera: SOLSTICE", *IEEE NSS/MIC*, 2001, pp. 1156-60.
W. Keyes, "The fan-beam gamma camera", *Phys. Med. Biol.*, pp. 489-493, vol. 20.
R.R. Gindi, et al., "imaging with rotating slit apertures and rotating collimators", *Med. Phys.*, 1982, pp. 324-339, vol. 9, No. 3.
P. Wanet, et al., "Evaluation of a rotating slit collimator in planar scintigraphy and in SPECT", *Proc. $39^{th}$ Annual Meeting SNM, J. Nucl. Med.*, 1992, p. 105, vol. 33, No. 5.
E.G. Hawman, et al., "Slat collimation for high sensitivity 2D and 3D emission imaging", *Proc. $40^{th}$ Annu. Meeting SNM. J. Nucl. Med.*, 1993, 10 p. vol. 34, No. 5.
M.Y. Chiu, et al., "Three dimensional reconstruction from planar projections", *J. Opt. Soc. Amer.*, pp. 755-762, vol. 70, No. 7.
M.A. Lodge, et al., "The experimental evaluation of a prototype rotating slat collimator for planar gamma camera imaging", *Phy. Med. Biol.*, 1995, pp. 426-448, vol. 40.
Moses, et al., "Design Studies for a PET Detector Module Using a PIN Photodiode to Measure Depth of Interaction", *IEEE Transactions on Nuclear Science NS-41*, 1994, pp. 1441-1445.

* cited by examiner

*Primary Examiner*—David Porta
*Assistant Examiner*—Marcus Taningco (57) ABSTRACT

A gamma camera having a scintillation detector formed of multiple rotating bar detector modules arranged in a ring configuration, with synchronized spin motion of each module. Such a camera can be used for both PET (coincidence) and single photon imaging applications. Image reconstruction is obtained using either an inverse 3-D Radon transform or a 3-D fan-beam algorithm.

20 Claims, 6 Drawing Sheets

NUCLEAR IMAGING SYSTEM USING ROTATING SCINTILLATION BAR DETECTORS WITH SLAT COLLIMATION AND METHOD FOR IMAGING USING THE SAME

BACKGROUND OF THE INVENTION

1. Field of the Invention

The present invention generally relates to nuclear medicine, and systems for obtaining nuclear medicine images of a patient's body organs of interest. In particular, the present invention relates to a novel detector configuration for nuclear medical imaging systems that are capable of performing either positron emission tomography (PET) or planar and single photon emission computed tomography (SPECT).

2. Description of the Background Art

Nuclear medicine is a unique medical specialty wherein radiation is used to acquire images that show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions that emanate from the body. One or more detectors are used to detect the emitted gamma photons, and the information collected from the detector(s) is processed to calculate the position of origin of the emitted photon from the source (i.e., the body organ or tissue under study). The accumulation of a large number of emitted gamma positions allows an image of the organ or tissue under study to be displayed.

Two basic types of imaging techniques are PET or "coincidence" imaging, and single photon imaging, also known as planar or SPECT imaging. PET imaging is fundamentally different from single photon imaging. In PET, events are detected from the decay or annihilation of a positron. When a positron is annihilated within a subject, two 511 KeV gamma rays are simultaneously produced which travel in approximately opposite (i.e., 180°) directions. Two scintillation detectors are positioned on opposite sides of the patient such that each detector will produce an electrical pulse in response to the interaction of the respective gamma rays with a scintillation crystal. In order to distinguish the detected positron annihilation events from background radiation or random events, the events must be coincident (i.e., both occur within a narrow time window) in each detector in order to be counted as "true" events. When a true event is detected, the line connecting the positions of the two points of detection is assumed to pass through the point of annihilation of the positron within the subject being imaged.

By contrast, single photon imaging, either planar or SPECT, relies on the use of a collimator placed in front of a scintillation crystal or solid state detector, to allow only gamma rays aligned with the holes of the collimator to pass through to the detector, thus inferring the line on which the gamma emission is assumed to have occurred. Both PET and single photon imaging techniques require gamma ray detectors that calculate and store both the position of the detected gamma ray and its energy.

Present day single photon imaging systems all use large area scintillation detectors (on the order of 2000 cm$^2$). Such detectors are made either of sodium iodide crystals doped with thallium (NaI(Tl)), or cesium iodide (CsI). Scintillations within the NaI crystal caused by absorption of a gamma photon within the crystal, result in the emission of a number of light photons from the crystal. The scintillations are detected by an array of photomultiplier tubes (PMTs) in close optical coupling to the crystal surface. Energy information is obtained by summing the signals from the PMTs that detected scintillation photons, and position information is obtained by applying a positioning algorithm to the quantitative signals produced by the PMT array. The original gamma-ray camera is described in U.S. Pat. No. 3,011,057 issued to Hal Anger in 1961.

The CsI camera is typically used with either a single silicon-based photodiode detector or an array of silicon-based photodiode detectors, which detect scintillation events emitted from the CsI crystal. CsI crystals are used where the relatively low cost, ruggedness and spectral response of the CsI crystal are desired in favor of alternative crystal materials such as NaI.

In PET imaging, scintillation crystals with short response times are required in order to properly detect the coincidence events with high timing resolution. Typically such crystals are chosen from among materials such as NaI, BGO, LSO and BaF$_2$. Detectors coupled to such crystals can be an array of PMTs, a single "position-sensitive" PMT ("PS-PMT"), or fast-response silicon-based photodiodes such as avalanche photodiodes.

Because the conventional Anger camera uses a thin planar sheet or disk of scintillation crystal material, it is necessary to cover the entire field of view of the crystal with light detectors such as PMTs or photodiodes. Additionally, because of the relatively small thickness dimension of the crystal (typically in the range of 0.5 to 2.5 cm) the sampling capability of such scintillation crystals is relatively low, in that a significant number of gamma photons emanating from an imaging subject will pass through the entire crystal without any interaction, and consequently cannot be detected for use is in constructing an image.

The bar detector is a specific configuration of scintillation detector that has been used in astronomical and high energy physics applications. The bar detector consists of an elongated scintillation crystal bar having a relatively small cross section. A photosensor such as a PMT is optically coupled to each end of the bar. The light from a gamma photon event within the scintillation crystal volume is detected by the two PMTs. The timing or signal information can be used to determine the location of the event in the bar. Additional bars can be placed next to each other for two dimensional detection.

An example of a proposed design for a PET detector module using a bar detector is given in Moses et al., "Design Studies for a PET Detector Module Using a PIN Photodiode to Measure Depth of Interaction," IEEE Transactions on Nuclear Science NS-41, pp. 1441–1445 (1994), incorporated herein by reference in its entirety. According to this design, a scintillation bar is coupled at one end to a PMT, and at the other end to a photodiode, in order to measure the depth of interaction (DOI) of the scintillation event in the bar.

In past bar detector experiments for physics and astronomy, NaI (and sometimes CsI) bars of up to 100 cm were used to detect gamma photons of up to 10 MeV. Positional resolution within the bar ranged from 1.5 cm at 200 keV to 2 cm at 10 MeV, although worse resolutions were reported. An energy resolution of 9.4% and a timing resolution of 10 ns at 662 keV and a 100 cm NaI bar were reported by a physics group for a balloon borne gamma telescope. Energy resolutions from other experiments were higher for the same energy gamma photon. These studies have cited geometry, bar size, light attenuation coefficient and electronic noise as the major factors in determining the spatial and energy resolution of bar detectors. However, the performance of bar detectors as designed in the prior art is insufficient for use in medical imaging applications.

A so-called rotating slit gamma camera is also known in the art, see, e.g., U.S. Pat. No. 4,514,632 to Barrett, issued Apr. 30, 1985. The rotating is slit camera has an elongated slit provided in an opaque disk located between the imaging object and the detector, such that scintillation event detection is obtained only in one dimension along the length of the slit (i.e., only a single spatial coordinate is obtained) at a time. The disk is rotated with respect to the detector to obtain spatial position information along other directions. One advantage of the rotating slit camera is that it eliminates the requirement for the inefficient simple collimator or pinhole apertures in the conventional Anger camera, which greatly restrict the percentage of gamma photons emanating from an imaging object that ultimately reach the detector.

Figure 1A:
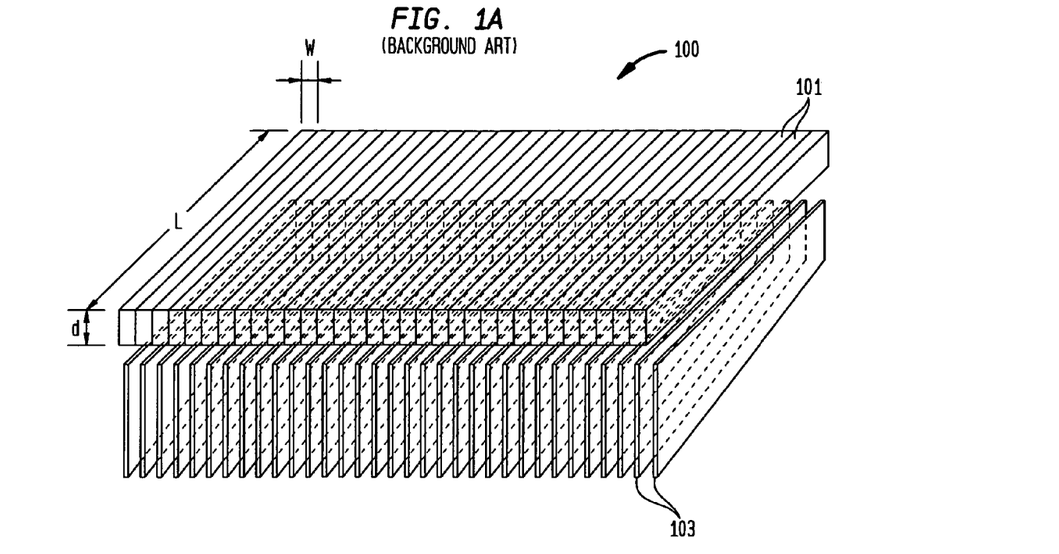
FIGS. 1a and 1b are isometric views of a rotating bar detector gamma camera with slat collimation, the principles of which are used in the present invention.
Figure 1B:
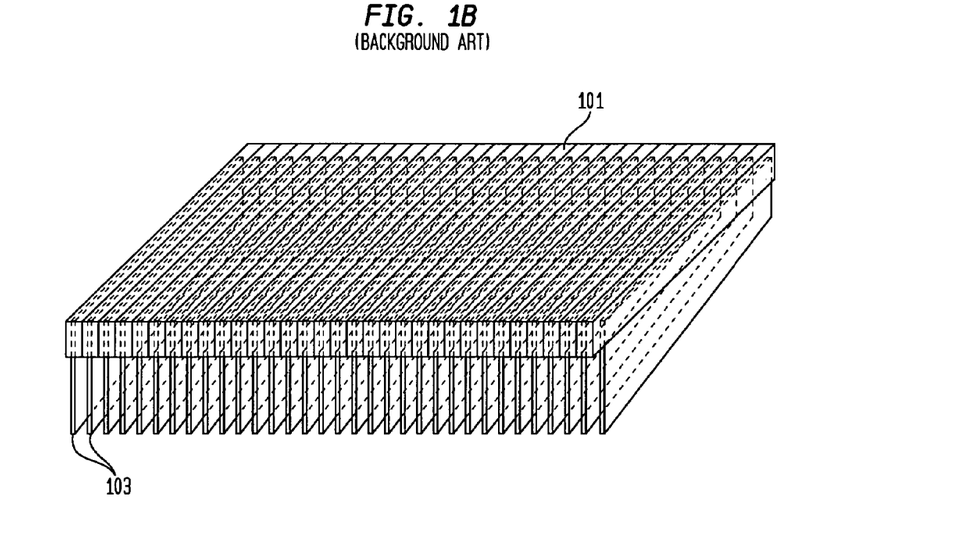
Figure 2:
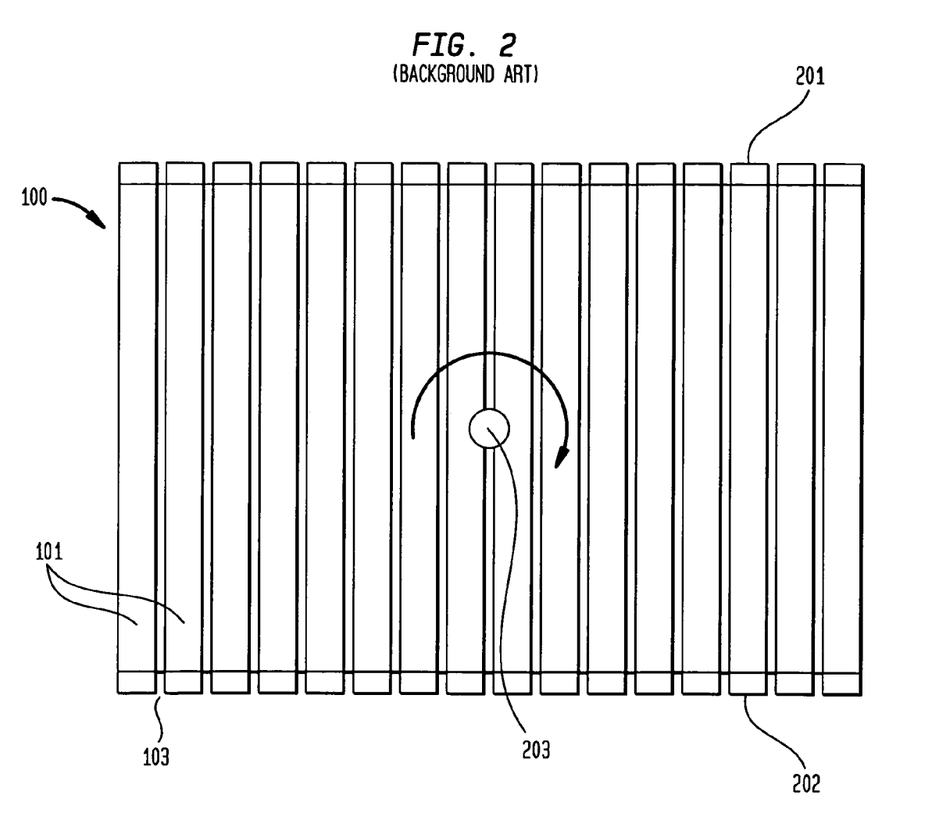
FIG. 2 is an end plan view of the rotating bar detector gamma camera of FIGS. 1a and 1b.
Figure 3:
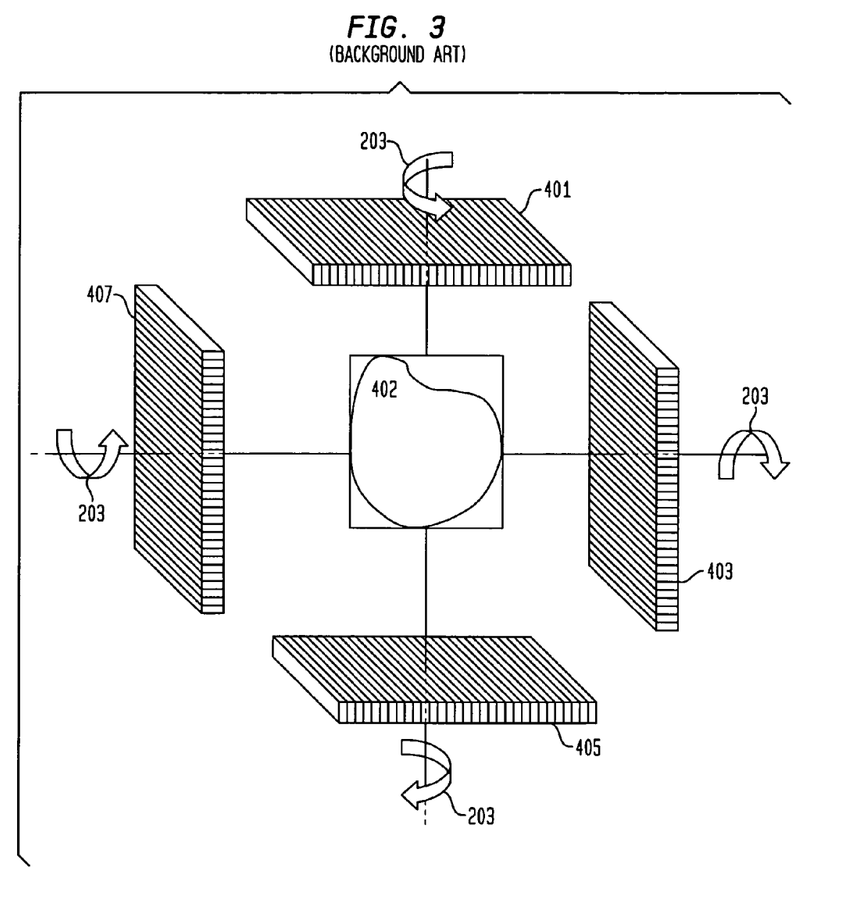
FIG. 3 is a diagram illustrating the use of the rotating bar detector camera according of FIGS. 1a–1b, to obtain tomographic images of a subject.

FIGS. 1–3 illustrate a rotating bar detector gamma camera with slat collimation as disclosed in co-pending U.S. patent application Ser. No. 10/633,935 by Ronald E. Malmin, and assigned to the same assignee herein. The rotating slat collimator detector uses planar integration as a method of image reconstruction. Only photons that are incident to the detector surface in the single direction parallel to the slats are collimated, and thus the detector generates a one-dimensional projection of a two-dimensional photon image. If such projections are acquired over a large number of different orientations, it becomes possible to reconstruct an image using the inversion of the 3-D Radon transform, as described in Chiu et al., "Three Dimensional Reconstruction from Planar Projections," J. Opt. Soc. Amer., Vol. 70, No. 7, pp. 755–762 (1980).

Referring to FIGS. 1a and 1b, a gamma camera detector 100 is constructed of a stack of scintillation bars 101. Each scintillation bar 101 is a narrow strip made of appropriate material such as CsI, NaI, LSO, LaBr3, LaCl3, etc.

Each bar 101 is collimated by a "slat" collimator 103, which collimates gamma photons in one dimension only (i.e., along the length of the bar).

Light photons generated by absorption of gamma rays within the bars 101 are collected at the ends of each bar by a pair of photodetectors 201, 202 (as shown in FIG. 2). The light photon detectors 201, 202 may be implemented as silicon drift detectors (SDDs), small area photodiodes or photodiode arrays, position-sensitive PMTs (PS-PMTs), or other solid-state photodetectors.

As shown in FIGS. 1a–b, the detector 100 is composed of a stack of narrow bar detector strips, each having the same length L, width w, and depth d. As illustrated, the width dimension w is significantly smaller than the depth d. The bar strips are each collimated by slat collimators 103. As shown, the slat 103 length and spacing matches the length and width of the bars 101. The entire slat collimator may be placed in front of the bar detector stack with respect to an imaging object (FIG. 1a), or the individual bars 101 may be located between slats 103 (FIG. 1b).

When placed adjacent to an imaging object that is emitting gamma radiation, each collimated bar will absorb gamma photons from a plane within the object. Gamma absorptions within each narrow strip produce a number of light photons that travel along the length of the bar strip in each direction, and are collected at the ends of the bar strip by the pair of SDDs 201, 202. Because the slat collimators collimate gamma photons in only one dimension (along their length), high position resolution is required in only the dimension perpendicular to the collimated bars. Consequently, a desirable value for the width w of the bar detector strips for contemplated medical imaging applications is on the order of 3 mm.

Because the slat collimators collimate gamma photons in only one dimension, the stack of bar detectors collects a set of planar integrals at each rotational position, as opposed to the line integrals that are collected by the conventional PMT arrays of the conventional Anger gamma camera. The bar detector stack 100 is positioned at a fixed gantry angle, and collects a sufficient number of events at its initial azimuthal position. The bar detector stack 100 then is rotated azimuthally about its central normal axis 203 as shown in FIG. 2. The bar detectors may be rotated through a total rotation angle of 180 degrees in increments, such as 3–5 degree rotational increments. The bar detectors then collect additional sets of planar events at each of the rotation angle increments. As shown in FIG. 3, the process is repeated at a number of different gantry angles 401, 403, 405, and 407 with respect to an imaging object 402 such as a patient undergoing medical is imaging. The resulting sets of planar integrals can be reconstructed to form a full tomographic image of the object 402.

Use of the stack of bar detector strips 100 in a rotating slat collimator configuration exhibits several desirable characteristics. As explained above, because of the one-dimensional nature of the detection, high positional resolution is required only in the dimension perpendicular to the slat collimators, and thus a narrow width bar detector strip on the order of 3 mm may be used, with light photon collection at each end. Position information along the bar is not required. Because light produced by scintillation events in each bar is channeled within the small area of each bar, extremely high count rates are possible without pileup from spatially separated events, especially if each bar detector is provided with its own detector readout electronics (in the case of PS-PMTs, each PS-PMT would detect light from multiple bars, with a corresponding reduction in the maximum count rate).

The reduction in pileup in turn allows the use of slower scintillator materials, such as CsI, which are well-matched to compact photodetectors such as photodiodes and SDDs. Because it is not necessary to determine spatial positioning of individual events along the length of the scintillation bars for image construction, no positioning calculations are required for imaging. Simple, fast positioning algorithms utilizing light collection ratios between the pair of photodetectors 201, 202 allow sufficient spatial resolution along the length of the bar to be utilized for the purpose of performing energy correction (e.g., energy correction based on spatial position of the event) to improve system energy resolution.

Because the depth of the bar detector does not affect spatial resolution, high spatial resolution is possible at high gamma ray energies, and the septa (slat collimators) can be made thick without causing septal artifacts in the resulting images.

There remains a need in the art to improve upon the design of a rotating bar detector gamma camera with slat collimation for specific imaging modalities.

SUMMARY OF THE INVENTION

The present invention solves the existing need by providing a gamma camera detector constructed of a bundle of bar scintillators with slat collimator having a configuration that maximizes geometric efficiency with respect to signal-tonoise ratio (SNR) of observed photon information, and is optimized for many imaging modalities, and in particular for emission CT scanning.

BRIEF DESCRIPTION OF THE DRAWINGS

The invention will become more clearly understood from the following detailed description in connection with the accompanying drawings, in which.

DETAILED DESCRIPTION OF THE PREFERRED EMBODIMENTS

Figure 4:
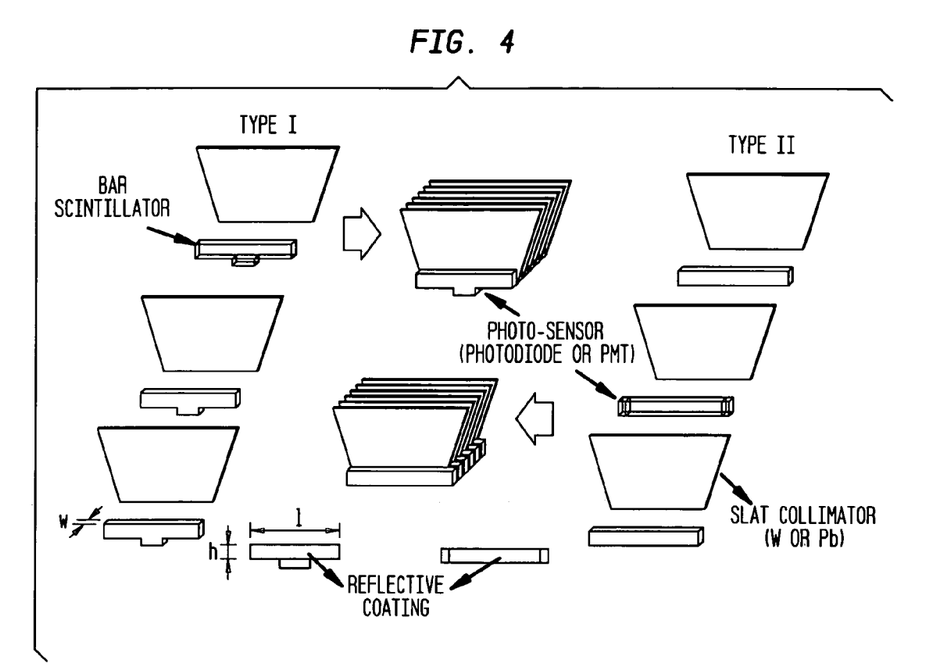
FIG. 4 shows structures of two types of basic bar detector modules according to embodiments of the present invention.

FIG. 4 shows the basic components of detector modules (i.e., a photosensor, collimator slats and a bar scintillator) and their assembled structures according to the present invention. Two different module types are proposed based on the coupling location of the photosensors on the bar scintillator. The type I module has a photosensor located at the middle-bottom of the scintillator, while the type II module has two photosensors, one mounted on each end. The type I and type II modules each have pros and cons in terms of electronic processing requirements, cost and performance characteristics.

In order to maximize light collection efficiency (LCE), each individual bar scintillator preferably is polished and wrapped with reflective materials such as MgO, $TiO_2$ or Teflon®, except for the area where the photosensor is coupled. The bar scintillator then is embedded between two elongated slats made from thin film tungsten or lead. This configuration prevents intercrystal scatter and photon crosstalk among scintillation crystals and ensures that each bar scintillator functions as an independent detector unit so that spatial resolution is guaranteed by the module design.

The physical parameters of the bar scintillator should be carefully selected since the dimensions and shape of the components control the cost/performance trade-off. For instance, the spatial resolution is determined by the space between slats, i.e., the width "w" of the bar scintillator as shown in FIG. 4; the bar scintillator thickness "h" determines the probability of gamma ray interaction; and the length "l" and module size determines the geometric efficiency of the system. The height and/or shape of the slats also greatly influence the geometric efficiency, the reconstructed image quality and the method of image reconstruction. Specific slat parameter selection is a consideration within the objectives of the system designer and can be accomplished with no more than routine selection and experimentation within the level of ordinary skill in this art.

Figure 5:
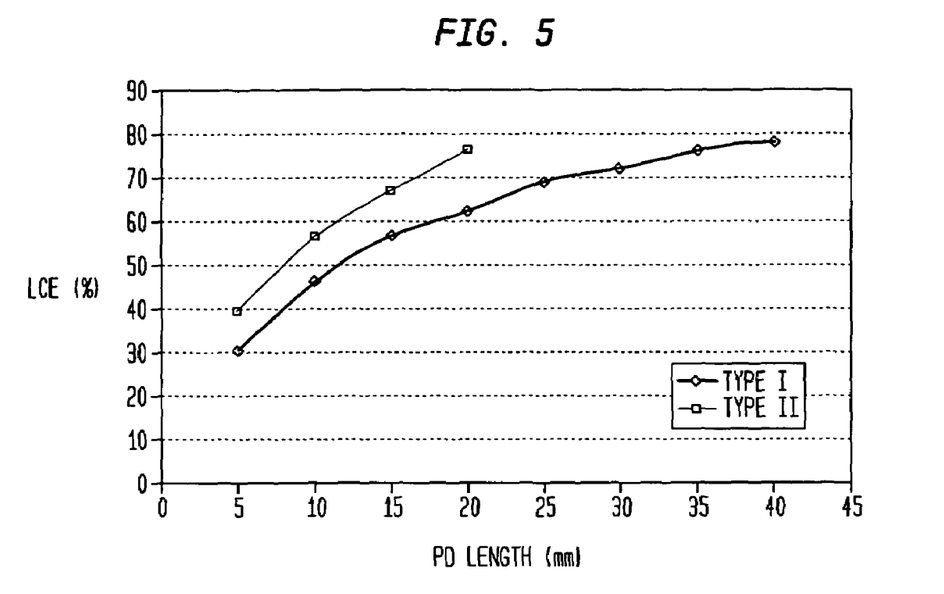
FIG. 5 is a graph illustrating light collection efficiency of the type I and type II modules shown in FIG. 4 as a function of sensor area.

The light yield properties of the bar scintillator play a key role in determining the energy/timing resolution and the position-invariant energy response of the module. FIG. 5 illustrates a Monte Carlo simulation result for type I and II modules as a function of the size of the detection area of the photosensor. The dimensions of the hypothetical bar scintillator were selected as 2×10 $mm^2$ cross section and 100 mm length, and the physical properties of CsI(Tl) crystal were used in the simulation.

All the surfaces except the photosensor coupling area were assumed to be slightly grounded (the angle between a given micro-facet and the mean surface was set to 10 degrees) and wrapped with Teflon® tape having a reflectivity of 98%. The width of the photosensor area was fixed to 2 mm (i.e., the same as that of the bar scintillator) and the length of the photosensor area was varied to investigate the effect on light collection efficiency as a function of photosensor size. For the type II module, identical photosensors are coupled at each end of the bar scintillator, and a summed value of the two sensors was recorded as total light output. Gamma ray interaction locations were simulated to be uniformly distributed over the bar scintillator with a mean depth of interaction at 2 mm from the entrance surface.

The result shows that the light collection efficiency (LCE) of both the type I and type II module is exponentially increased as the detection area is increased. The type II module was found to be the better configuration in collecting light, taking into account the cost of additional electronics. Where a typical PN junction type photodiode is used as a photosensor, electronic noise increases monotonically as detection area increases. Therefore, the optimum detector size must be considered at the point where the signal-to-noise ratio (SNR) is maximized.

Figure 6:
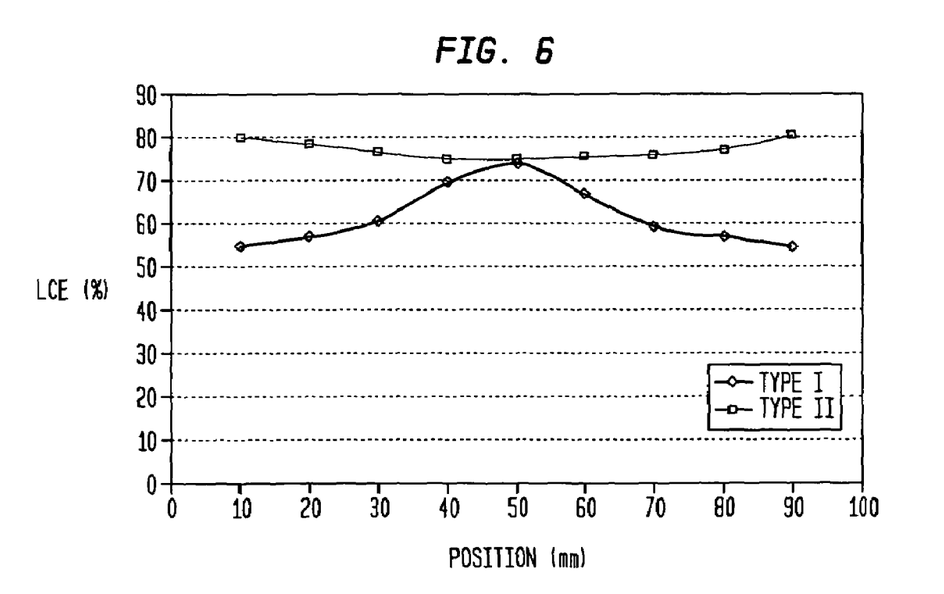
FIG. 6 is a graph illustrating light collection efficiency of the type I and type II modules shown in FIG. 4 as a function of the incident position of a gamma photon.

FIG. 6 shows the position-dependent LCE property of the type I and II modules as a function of gamma photon incidence position. A well-collimated point source was scanned over points spaced 10 mm apart from each other in the long direction of the bar scintillator. The dimensions and surface conditions of the bar scintillator were the same as the setup for the simulation of FIG. 5.

One photosensor of size 2×20 $mm^2$ was coupled at the middle-bottom of the bar scintillator for the type I module, and two photosensors of size 2×10 $mm^2$ were coupled at the ends of the bar scintillator for the type II module. The results as shown in FIG. 6 indicate that the type II module has better uniformity and higher LCE than the type I module. Based on analogical interpretation, if the mean energy resolution of the module is 10%, the standard deviations are 0.94 and 0.21, i.e., 10±0.94% and 10±0.21% fluctuation of energy resolution, for the type I module and the type II module, respectively.

In addition, the type II module can provide additional positioning information by employing bar detector statistics-based positioning estimation. One example estimator is as follows:

$$\hat{x} = \arg\min_{\forall x} \min_{x=\hat{x}} \left( \frac{(R - \mu_R(x))^2}{\sigma_R^2(x)} \right) \quad (1)$$

where R is the ratio between the energy signals of the photodetectors for a given event, i.e., $$R = \frac{E_1 - E_2}{E_1 + E_2},$$

and $\mu_R(x)$ and $\sigma_R^2(x)$ are the mean and variance of the ratio R at a given location x, respectively. The $\mu_R(x)$ and $\sigma_R^2(x)$ must be pre-computed and stored in a look-up table.

Figure 7:
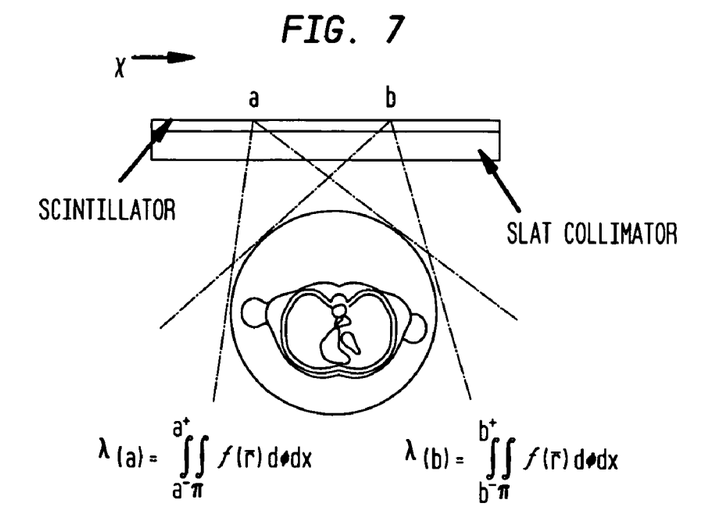
FIG. 7 is a diagram showing three dimensional reconstruction of an image from integration of planar images.

It might be subject to debate whether having additional positioning information along the long direction of a bar detector is beneficial for the quality of a reconstructed image. For instance, consider two planar integrations $\lambda(a)$ and $\lambda(b)$ at points 'a' and 'b' respectively on the bar detector as shown in FIG. 7.

$$\text{where } \lambda(a) = \int_{a^+}^{a^-} \int_\pi f(\vec{r}) d\phi dx \text{ and } \lambda(b) = \int_{b^+}^{b^-} \int_\pi f(\vec{r}) d\phi dx.$$

$f(\vec{r})$ represents the photon distribution of an object in three-dimensional space.

From the conventional 3-D inverse Radon transform point of view, the additional positioning information along the x-direction is meaningless because $\lambda(a)$ and $\lambda(b)$ are superimposed over each other when they are binned. However, if fan-beam type 3-D planar reconstruction algorithms are developed, the integration $\lambda(a)$ may be differentiated from $\lambda(b)$ and they would be regarded as independent variables. The details of the image reconstruction issue will not be further discussed as they are beyond scope of this invention.

In order to reconstruct an image from planar projections using the inverse of the 3-D Radon transform, a sufficient amount of projections need to be collected at various orientations. In the prior art (see, e.g., U.S. Pat. No. 4,514,632, supra), this status was achieved by spanning the slit collimation detector itself while also turning the gantry such that the detector rotated about an object. This acquisition configuration is not favorable for detectors with a relatively smaller field of view (FOV) than that of the conventional bulky detectors.

Figure 8:
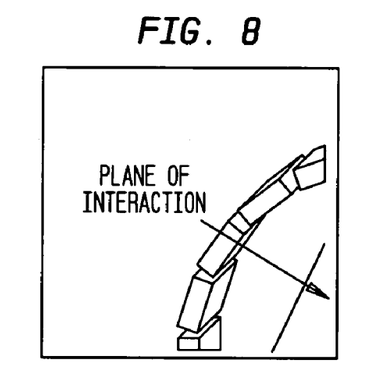
FIG. 8 is a diagram illustrating one preferred embodiment of an image acquisition detector according to the present invention.

One preferred embodiment of an acquisition system configuration according to the present invention is shown in FIG. 8. The proposed detector module is represented by element 80 and a multiplicity of modules 80 are arranged to construct a ring structure. Each detector module spins about an axis 82, and the motion of all modules must be synchronized. This can be accomplished by engaging each individual gear mounted at the center of the spin-axis of each module with a ring gantry gear. This set-up not only eliminates complicated and expensive individual spin motion control but also guarantees precise synchronization of spinning motion among the modules. A wobble and/or tilt motion also can be imparted to the detector ring to increase sampling density and/or to scan a target organ at optimum view angles.

The detector ring configuration provides several advantages over conventional one or two detector gantry system setups. First, throughput is increased by shortening patient scan time; second, gantry rotation motion is eliminated, thereby extending mechanical component lifetime and reducing maintenance requirements; third, geometric efficiency is optimized with respect to SNR; and finally, coincidence imaging is possible using the same configuration as used for single photon imaging, by recording an event only if annihilation photons are detected simultaneously by bar scintillator modules that are co-located on a defined 'plane of interaction'. Examples of possible simultaneous detection planes of interaction are illustrated in FIG. 8.

If the number of planes of interaction is increased by additional ring gantry motions such as wobble and/or tilt and/or the plane of interaction as is shown in FIG. 8 is subdivided into smaller planes by extra positioning information along the bar scintillator, the quality of the reconstructed images becomes comparable to that of a dedicated PET system.

A Monte Carlo simulation was conducted using a SimSET package to evaluate the geometric efficiency improvement of the proposed slat collimation detector module over that of the conventional parallel-hole collimation detector. A digital anthropomorphic phantom was constructed from the Zubal photon. The relative activity concentration of organs is listed in table 1.

TABLE 1

Relative activity concentration of Tc$^{99m}$ Sestamibi cardiac study.

| | Organ | | | | | |
|---|---|---|---|---|---|---|
| | Heart | Lung | Liver | Kidney | Spleen | Sternum |
| Relative activity | 1.0 | 0.03 | 0.69 | 0.84 | 0.96 | 0.12 |

This configuration was specified to approximate a typical clinic cardiac Tc99m Sestamibi study. The injected dose was simulated to be 9 mCi. Energy resolution was modeled by a simple Gaussian blur of the detected photon energy, with a FWHM of 9% at 140 keV.

A conventional gamma camera detector, modeled after an Ecam system (Siemens Medical Solutions USA, Hoffman Estates, Ill.), was simulated with axial and trans-axial detector lengths of 40 cm and 50 cm, respectively, and equipped with a low energy general purpose (LEGP) collimator. For the slat collimation bar detector, axial and trans-axial size was 10 cm by 10 cm, and a slat collimator, 0.3 mm thick, 10 cm long, 4 cm tall, with 2 mm separation between septa was placed in front of the detector. For both cases, 10 mm thick NaI(Tl) crystal was modeled as the detector scintillator.

The inner radius from the center of the object to the surface of the detector block was set to 34 cm for both cases. The events are binned into primary and scatter events separately.

Table 2 summarizes the geometric efficiency and scatter fraction of conventional system and proposed slat detector for the all energy range and 10% photo peak case as well.

TABLE 2

Geometric efficiency and scatter fraction
of the conventional and slat detector.

| Energy | Detector | Primary | Scatter | SF (%) |
|---|---|---|---|---|
| All energy | R-slat | 11.9 kcps | 59.8 kcps | 83 |
| | Ecam | 5.2 kcps | 21.1 kcps | 80 |
| 10% photo peak | R-slat | 8.9 kcps | 3.5 kcps | 28 |
| | Ecam | 4.0 kcps | 1.5 kcps | 26 |

Note that the volume of the scintillator of the conventional detector was 20 times larger than that of the slat detector for this comparison. The result shows that the proposed slat detector module realized increases in geometric efficiency of about 40 times while maintaining a scatter fraction similar to that of the conventional system with LEGP collimator.

Figure 9:
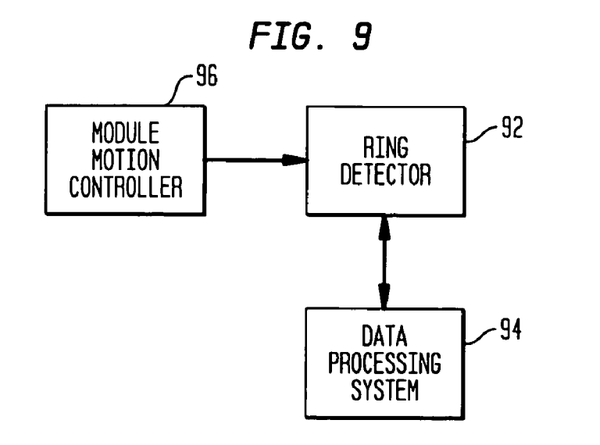
FIG. 9 is a block diagram of an imaging system using the image acquisition detector according to an embodiment of the present invention.

FIG. 9 is a block diagram showing a complete imaging system according to the present invention. The ring detector 92 is electrically coupled to a data processing system 94. A spin-motion controller 96 is coupled to the detector 92 to control spin-motion of the modules, including synchronization thereof. Data acquired by detector system 92 is inputted to processing system 94 for processing into viewable images. For example, processing system 94 may include a microprocessor, random access memory, data storage, a display monitor, user interface and input devices, etc. The data storage may include various image processing application including the inverse 3-D Radon transform.

The invention having been described, it will be apparent to those skilled in the art that the same may be varied in many ways without departing from the spirit and scope of the invention. Any and all such modifications are intended to be included within the scope of the following claims.

What is claimed is:

1. A ring detector radiological image acquisition system, comprising:
a plurality of detector modules arranged in a ring configuration, with each detector module comprising a plurality of bar detector strips made of scintillating material, arranged in a stack configuration, at least one photodetector coupled to at least one side of said stack, and a slat collimator including a plurality of elongated slats, for collimating each of said plurality of bar detector strips to receive gamma photons in only a single dimension;
each of said plurality of detector modules having a central axis and being controlled to spin about its central axis in a synchronized manner with the others of said plurality of detector modules, such that radiological image information sufficient to construct a clinically significant image is acquired from a subject located substantially in the center of said ring configuration simultaneously by said plurality of detector modules without rotation of said ring.

2. The ring detector image acquisition system of claim 1, wherein each bar detector strip contains a photodetector mounted on a longer dimension side thereof.

3. The ring detector image acquisition system of claim 1, wherein each bar detector strip contains a photodetector mounted on each shorter dimension side thereof.

4. The ring detector image acquisition system of claim 2, wherein said photodetectors comprise photomultiplier tubes.

5. The ring detector image acquisition system of claim 3, wherein said photodetectors comprise photomultiplier tubes.

6. The ring detector image acquisition system of claim 2, wherein said photodetectors comprise photodiodes.

7. The ring detector image acquisition system of claim 3, wherein said photodetectors comprise photodiodes.

8. The ring detector image acquisition system of claim 1, further comprising a controller for controlling spin motion of said detector modules to be in synchronization.

9. The ring detector image acquisition system of claim 1, further comprising a processing system for reconstructing a radiological image using an inverse 3-D transform on image information received from said detector.

10. The ring detector image acquisition system of claim 1, further comprising a processing system for reconstructing a radiological image using a 3-D fan-beam reconstruction algorithm on image information received from said detector.

11. A method of obtaining a radiological image of a subject, comprising the steps of:
using a ring detector having plurality of detector modules arranged in a ring configuration, with each detector module comprising a plurality of bar detector strips made of scintillating material, to acquire radiological image data from said subject located substantially in the center of said ring detector simultaneously by said plurality of detector modules without rotation of said ring; and
processing said radiological image data using a 3-D reconstruction algorithm.

12. The method of claim 11, wherein each detector module includes a bar detector strip containing a photodetector mounted on a longer dimension side thereof.

13. The method of claim 11, wherein each detector module includes a bar detector strip containing a photodetector mounted on each shorter dimension side thereof.

14. The method of claim 12, wherein said photodetectors comprise photomultiplier tubes.

15. The method of claim 13, wherein said photodetectors comprise photomultiplier tubes.

16. The method of claim 12, wherein said photodetectors comprise photodiodes.

17. The method of claim 13, wherein said photodetectors comprise photodiodes.

18. The method of claim 11, further comprising the step of controlling spin motion of said detector modules to be in synchronization.

19. The method of claim 11, wherein the step of reconstructing a radiological image comprises using an inverse 3-D transform on image information received from said detector.

20. The method of claim 11, wherein the step of reconstructing a radiological image comprises using a 3-D fan-beam reconstruction algorithm on image information received from said detector.

* * * * *